(12) United States Patent
Park et al.

(10) Patent No.: US 11,898,882 B2
(45) Date of Patent: *Feb. 13, 2024

(54) APPARATUS AND METHOD FOR CALIBRATION OF BIO-INFORMATION ESTIMATION MODEL, AND BIO-INFORMATION ESTIMATING APPARATUS

(71) Applicant: SAMSUNG ELECTRONICS CO., LTD., Suwon-si (KR)

(72) Inventors: Chang Soon Park, Chungju-si (KR); Ui Kun Kwon, Hwaseong-si (KR); Seung Keun Yoon, Seoul (KR); Dae Geun Jang, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

This patent is subject to a terminal disclaimer.

(21) Appl. No.: 17/984,880

(22) Filed: Nov. 10, 2022

(65) Prior Publication Data

US 2023/0065255 A1 Mar. 2, 2023

Related U.S. Application Data

(63) Continuation of application No. 16/409,190, filed on May 10, 2019, now Pat. No. 11,525,714.

(30) Foreign Application Priority Data

Jul. 27, 2018 (KR) .................. 10-2018-0088096

(51) Int. Cl.
   *G08B 21/04* (2006.01)
   *G01D 18/00* (2006.01)
   *A61B 5/021* (2006.01)

(52) U.S. Cl.
   CPC .............. *G01D 18/00* (2013.01); *A61B 5/021* (2013.01); *A61B 2560/0223* (2013.01)

(58) Field of Classification Search
   USPC ......... 340/539.12, 539.15, 539.22, 575, 665, 340/691.3, 5.82, 4.1, 4.11, 4.13
   See application file for complete search history.

(56) References Cited

U.S. PATENT DOCUMENTS 7,455,643 B1   11/2008   Li et al.
8,560,245 B2   10/2013   Li et al.
(Continued)

FOREIGN PATENT DOCUMENTS

JP   1997-299339 A   11/1997
JP   2012-125281 A   7/2012
(Continued)

OTHER PUBLICATIONS

Sandrine C. Millasseau et al., "The Vascular Impact of Aging and Vasoactive Drugs: Comparison of Two Digital Volume Pulse Measurements", American Journal of Hypertension, vol. 16, No. 6, Jun. 2003, pp. 467-472 (6 pages total).
(Continued)

*Primary Examiner* — Daniel Previl
(74) *Attorney, Agent, or Firm* — Sughrue Mion, PLLC

(57) ABSTRACT

An apparatus for calibration of a bio-information estimation model includes a sensor configured to obtain a bio-signal from an object in a reference interval; a feature extractor, implemented by at least one processor, configure to extract a reference feature value from the bio-signal; and a calibrator, implemented by the at least one processor, configured to determine whether a condition is satisfied based on at least one of the reference feature value and an offset value, and based on determining that the condition is satisfied, config-
(Continued)

ured to calibrate the bio-information estimation model based on the reference feature value and the offset value.

18 Claims, 20 Drawing Sheets

(56) References Cited

U.S. PATENT DOCUMENTS

| | | | |
|---|---|---|---|
| 9,259,160 | B2 | 2/2016 | Watson et al. |
| 9,408,575 | B2 | 8/2016 | Bordoley et al. |
| 9,433,361 | B2 | 9/2016 | Hyogo et al. |
| 9,612,656 | B2 | 4/2017 | Sztuk et al. |
| 11,525,714 | B2 * | 12/2022 | Park ................ G16H 40/40 |
| 2011/0054328 | A1 | 3/2011 | Hyogo et al. |
| 2011/0066043 | A1 | 3/2011 | Banet et al. |
| 2012/0116175 | A1 | 5/2012 | Al-Ali et al. |
| 2015/0099953 | A1 | 4/2015 | Baker, Jr. |
| 2016/0057599 | A1 * | 2/2016 | Lim ................ H04W 52/223 |
| | | | 455/404.1 |
| 2017/0042433 | A1 | 2/2017 | Noh et al. |
| 2017/0119263 | A1 | 5/2017 | Hill |
| 2017/0172431 | A1 | 6/2017 | Kim et al. |
| 2018/0014791 | A1 | 1/2018 | Montgomery et al. |
| 2018/0129939 | A1 * | 5/2018 | Yang ..................... G06N 3/04 |
| 2018/0199832 | A1 | 7/2018 | Mori et al. |
| 2018/0294564 | A1 | 10/2018 | Kim |
| 2019/0038218 | A1 * | 2/2019 | Chang ................. A61B 5/746 |
| 2019/0083010 | A1 * | 3/2019 | Lee .................. A61B 5/14546 |
| 2019/0154656 | A1 * | 5/2019 | Bae ................... G01N 21/3103 |
| 2019/0252079 | A1 | 8/2019 | Constantin et al. |

FOREIGN PATENT DOCUMENTS

| | | |
|---|---|---|
| JP | 5443899 B2 | 3/2014 |
| JP | 2017-056107 A | 3/2017 |
| JP | 2018-15061 A | 2/2018 |
| KR | 10-1503604 B1 | 3/2015 |

OTHER PUBLICATIONS

Youngzoon Yoon & Gilwon Yoon, "Nonconstrained Blood Pressure Measurement by Photoplethysmography", Journal of the Optical Society of Korea, vol. 10, No. 2, Jun. 2006, pp. 91-95 (5 pages total).

Communication dated Jan. 3, 2020, issued by the European Patent Office in counterpart European Application No. 19188034.3.

* cited by examiner

APPARATUS AND METHOD FOR CALIBRATION OF BIO-INFORMATION ESTIMATION MODEL, AND BIO-INFORMATION ESTIMATING APPARATUS

CROSS-REFERENCE TO RELATED APPLICATION(S)

This application is a continuation application of U.S. application Ser. No. 16/409,190, filed May 10, 2019, which claims priority from Korean Patent Application No. 10-2018-0088096, filed on Jul. 27, 2018, in the Korean Intellectual Property Office, the entire disclosure of which is incorporated herein by reference for all purposes.

BACKGROUND

1. Field

Apparatuses and methods consistent with example embodiments relate to apparatuses and methods for calibration of a bio-information estimation model, and a bio-information estimating apparatus.

2. Description of the Related Art

With the aging population, soaring medical costs, and a lack of medical personnel for specialized medical services, research has been actively conducted on information technology (IT)-medical convergence technologies, in which IT and medical technology are combined. Particularly, monitoring of the health condition of the human body is not limited to medical institutions, but applies to mobile healthcare fields that may monitor a user's health condition in daily life anywhere such as home or office and anytime. Typical examples of bio-signals, which indicate the health condition of individuals, include an electrocardiography (ECG) signal, a photoplethysmogram (PPG) signal, an electromyography (EMG) signal, and the like, and various bio-signal sensors have been developed to measure these signals in daily life. Particularly, a PPG sensor may estimate blood pressure of a human body by analyzing a shape of pulse waves which reflect cardiovascular status and the like.

According to studies on the PPG signal, the entire PPG signal is a superposition of propagation waves starting from the heart toward the distal end portions of the body and reflection waves returning back from the distal end portions. Further, it has been known that information for estimating blood pressure may be obtained by extracting various features associated with the propagation waves or the reflection waves.

SUMMARY

According to an aspect of an example embodiment, there is provided an apparatus for calibrating a bio-information estimation model, the apparatus including: a sensor configured to obtain a bio-signal from an object in a reference interval; a feature extractor, implemented by at least one processor, configure to extract a reference feature value from the bio-signal; and a calibrator, implemented by the at least one processor, configured to determine whether a condition is satisfied based on at least one of the reference feature value and an offset value, and based on determining that the condition is satisfied, configured to calibrate the bio-information estimation model based on the reference feature value and the offset value.

The calibrator may be configured to determine whether the condition is satisfied based on a result of comparing the reference feature value with a feature threshold.

The feature threshold may be set based on at least one statistical value of feature values obtained from a plurality of objects and a statistical value of feature values of bio-signals obtained from the plurality of objects in a plurality of intervals.

The calibrator may be configured to determine whether the condition is satisfied based on a result of comparison between the offset value and a reference bio-information value.

The apparatus may further include an interactor, implemented by the at least one processor, configured to receive the reference bio-information value from a user.

The apparatus may further include an interactor, implemented by the at least one processor, configured to output an inquiry to a user and receive a response to the inquiry from the user.

The interactor may be configured to output the inquiry relating to an action made by the object during a predetermined period of time prior to the reference interval.

The calibrator may be configured to determine whether the condition is satisfied based on the response to the inquiry.

The apparatus may further include an interactor, implemented by the at least one processor, configured to output information about an action to be made by the object during a predetermined period of time prior to performing calibration of the bio-information estimation model.

The action to be made by the object may include having a resting state before a meal.

The apparatus may further include an interactor, implemented by the at least one processor, the interactor configured to, based on determining that the condition is not satisfied, guide the object to request recalibration, and/or to provide information indicating that calibration is not to be performed.

The apparatus may further include a communication interface configured to receive the offset value from an external device.

The apparatus may further include an interactor, implemented by the at least one processor, configured to receive the offset value from a user.

According to an aspect of an example embodiment, there is provided a method of calibrating a bio-information estimation model including: obtaining a bio-signal from an object in a reference interval; extracting a reference feature value from the bio-signal; determining whether a condition is satisfied based on at least one of the reference feature value and an offset value; and based on determining that the condition is satisfied, calibrating the bio-information estimation model based on the reference feature value and the offset value.

The determining whether the condition is satisfied may include determining whether the condition is satisfied based on a result of comparing the reference feature value with a predetermined feature threshold.

The determining whether the condition is satisfied may include determining whether the condition is satisfied based on a result of comparison between the offset value and a reference bio-information value.

The method may further include receiving the reference bio-information value from a user.

The method may further include outputting, through an interface, an inquiry to a user and receiving a response to the inquiry from the user.

The method may further include outputting an inquiry about an action made by the object during a predetermined period of time prior to the reference interval, wherein the determining whether the condition is satisfied includes determining whether the condition is satisfied based on a response to the inquiry.

The method may further include, based on determining that the condition is not satisfied, guiding the object to request recalibration, and/or providing information indicating that calibration is not to be performed.

The method may further include receiving the offset value corresponding to the reference interval from at least one of an external device and a user.

According to an aspect of an example embodiment, there is provided an apparatus for calibrating a bio-information estimation model, the apparatus including: a sensor configured to obtain a bio-signal from an object in a reference interval; a feature extractor, implemented by at least one processor, configure to extract a reference feature value from the bio-signal; and a calibrator, implemented by the at least one processor, configured to determine whether a condition is satisfied based on at least one of the reference feature value and an offset value, and based on determining that the condition is satisfied, configured to calibrate the bio-information estimation model based on sets of a plurality of reference feature values and a plurality of offset values respectively obtained in a first reference interval to a second reference interval.

The calibrator may be configured to: obtain the plurality of reference feature values based on a statistical value including at least one of a mean value and a weighted average of the plurality of reference feature values, or a value calculated by performing a first pre-defined function on the plurality of reference feature values; and obtain the plurality of offset values based on a statistical value including at least one of a mean value and a weighted average of the plurality of offset values, or a value calculated by performing a pre-defined second function on the plurality of offset values.

The apparatus may further include memory configured to store the reference feature value and the offset value corresponding to the reference interval, based on the at least one of which it is determined that the condition is satisfied.

The second reference interval may precede the first reference interval.

The second reference interval may be an interval in which initial calibration is performed.

According to an aspect of an example embodiment, there is provided an apparatus for estimating bio-information, the apparatus including: a sensor configured to obtain a bio-signal from an object; a feature extractor, implemented by at least one processor, configure to extract a feature value from the bio-signal; and a calibrator, implemented by the at least one processor, configured to determine whether a condition is satisfied based on at least one of a reference feature value and an offset value, the reference feature value being extracted from the bio-signal in a reference interval, and based on determining that the condition is satisfied, configured to calibrate a bio-information estimation model based on the reference feature value and the offset value; and a bio-information estimator, implemented by the at least one processor, configured to estimate the bio-information based on the calibrated bio-information estimation model and the feature value extracted from the bio-signal in a bio-information estimation interval.

The apparatus may further include an interactor, implemented by the at least one processor, configured to output an inquiry to a user and receive a response to the inquiry from the user, the inquiry being related to at least one of the offset value and an action made by the object during a predetermined period of time prior to performing calibration.

The apparatus may further include a communication interface configured to receive the offset value corresponding to the reference interval from an external device.

The apparatus may further include a calibration controller implemented by the at least one processor, configured to control the calibrator by determining whether to perform calibration based on at least one of a result of the estimating the bio-information, reference information.

The apparatus may further include an interactor, implemented by the at least one processor, configured to output information associated with a result of at least one calibration of the bio-information estimation model and estimation of the bio-information.

BRIEF DESCRIPTION OF THE DRAWINGS

The above and/or other aspects will be more apparent by describing certain example embodiments with reference to the accompanying drawings, in which.

DETAILED DESCRIPTION

Figure 1:
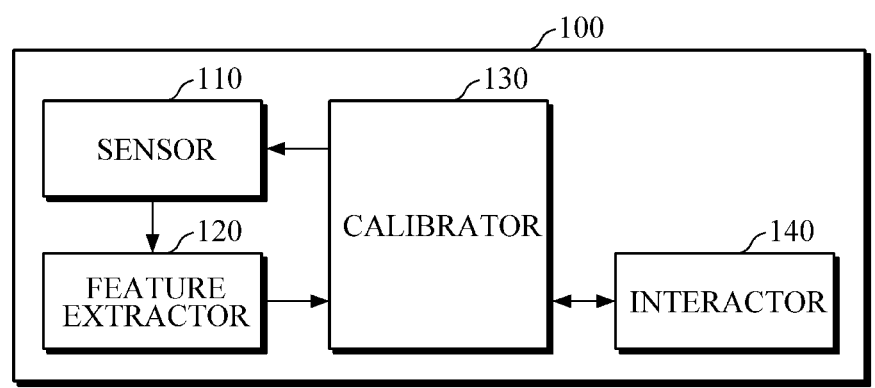
FIG. 1 is a block diagram illustrating a calibration apparatus according to an example embodiment.

Details of example embodiments are included in the following detailed description and drawings. Aspects of example embodiments will be more clearly understood from the following description with reference to the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, example embodiments of apparatuses and methods for calibration of a bio-information estimation model will be described in detail with reference to the accompanying drawings.

Various example embodiments of the calibration apparatus, which will be described below, may be embedded in a portable wearable device, a smart device, and the like. For example, examples of the devices may include: a wearable device manufactured in various types such as a smart watch, a smart band-type device, a headphone-type device, a headband-type device, and the like; and a mobile device such as a smartphone, a tablet PC, and the like, but the devices are not limited thereto.

Figure 2A:
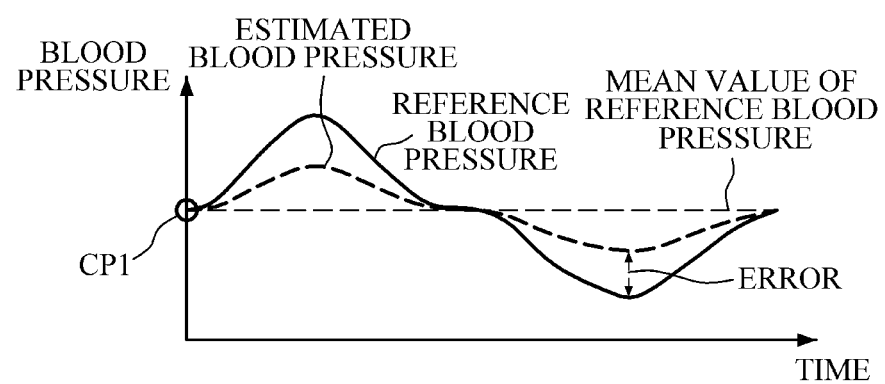
FIGS. 2A and 2B are diagrams explaining calibration.
Figure 2B:
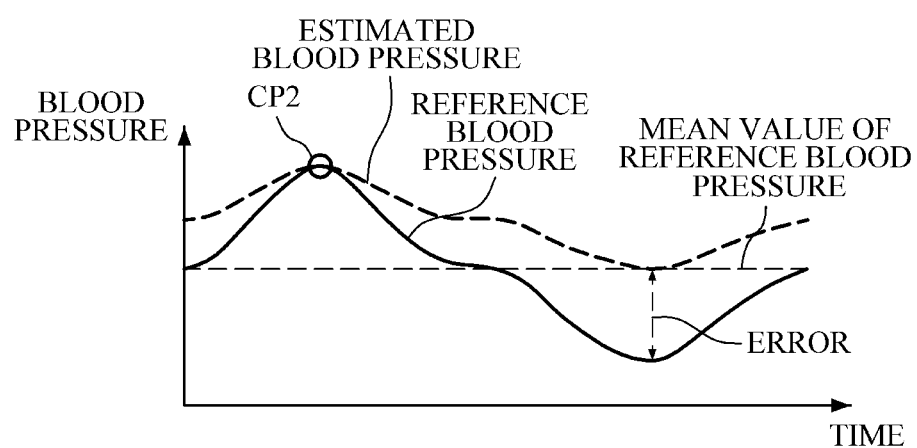
Figure 3:
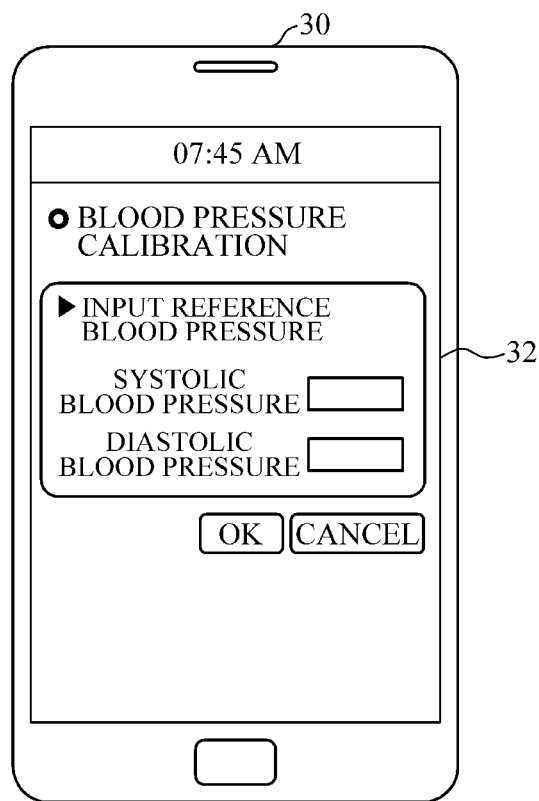
FIG. 3 is a diagram illustrating an example of interaction with a user.

FIG. 1 is a block diagram illustrating a calibration apparatus according to an example embodiment. FIGS. 2A and 2B are diagrams explaining calibration. FIG. 3 is a diagram illustrating an example of interaction with a user.

According to an example embodiment, a bio-information estimation model may be calibrated so that a bio-information estimating apparatus may estimate bio-information more accurately. In this case, bio-information may include blood pressure, heart rate, vascular age, arterial stiffness, aortic pressure waveform, stress index, degree of fatigue, and the like, but is not limited thereto. For convenience of explanation, the following description will be given by using blood pressure as an example of bio-information.

For accurate estimation of bio-information, a blood pressure estimation model may be generally calibrated by using information on one or more features obtained from a pulse wave signal in an initial stable state, and/or reference blood pressure information obtained over a period of time which is the same as or similar to a period of time when the features are extracted. In this case, the reference blood pressure information may refer to blood pressure values obtained using a blood pressure measuring apparatus which may measure an actual blood pressure in the blood vessels by using a cuff and the like.

However, a calibration result may not be accurate under various circumstances. For example, an unstable bio-signal may be measured due to occurrence of noise in a calibration interval (e.g., an interval in which calibration is performed), or an unstable contact state between a sensor and a human body; and as a result, features may not be extracted stably from the bio-signal. In another example, a reference blood pressure value may be inaccurately measured in a calibration interval. In the case where a blood pressure estimation model is calibrated based on the inaccurate reference blood pressure value, accuracy of estimating blood pressure may be reduced.

In yet another example, even when a reference blood pressure value is accurately measured, if the reference blood pressure value is excessively high or low and calibration is performed based on the excessively high or low value, accuracy of an estimated blood pressure value may be reduced. For example, FIG. 2A illustrates an example of performing calibration based on a mean value of reference blood pressure values measured over a predetermined period of time, and estimating blood pressure based on a calibration result. FIG. 2B illustrates an example of performing calibration based on a maximum value of reference blood pressure values measured over a predetermined period of time, and estimating blood pressure based on a calibration result.

Referring to FIG. 2B, when calibration is performed at a point CP2, at which an actual blood pressure value measured during daily life activities is a maximum value, an error between the actual blood pressure value and an estimated blood pressure value may become very large. By contrast, referring to FIG. 2A, when calibration is performed at a point CP1, at which an actual blood pressure value measured during daily life activities is a mean value, an average error between the actual blood pressure value and the estimated blood pressure value may be relatively small.

According to example embodiments, an apparatus for calibrating a bio-information estimation model is provided which may improve accuracy of the estimated blood pressure even under various circumstances.

Referring to FIG. 1, an apparatus 100 for calibrating a bio-information estimation model includes a sensor 110, a feature extractor 120, a calibrator 130, and an interactor 140. Here, the feature extractor 120, the calibrator 130, and the interactor 140 may be components included in one or more processors.

The sensor 110 measures a bio-signal from an object. In this case, the bio-signal may be a photoplethysmogram (PPG) signal. However, the bio-signal is not limited thereto, and may include various bio-signals, such as an electrocardiography (ECG) signal, a photoplethysmogram (PPG) signal, and an electromyography (EMG) signal, and the like, which may be modeled by adding together a plurality of waveform components.

For example, the sensor 110 may include: one or more light sources which emit light onto an object; and one or more detectors which detect light emitted onto the object and scattered or reflected from a body tissue of the object. In this case, the light source may include at least one of a light emitting diode (LED), a laser diode (LD), a fluorescent body, and the like, and the detector may include a photo diode, but the light source and the detector are not limited thereto. One or more light sources may emit light of different wavelengths, and may be positioned at different distances from the detector.

In response to a request for calibration, the sensor 110 may measure a reference bio-signal in a reference interval. In this case, the reference interval may refer to a time interval for performing calibration and may be, for example, a predetermined time interval on an empty stomach before a meal. However, the reference interval is not limited thereto, and may be a predetermined time interval after a time when a request for calibration is received.

The feature extractor 120 may extract one or more reference features from the reference bio-signal. For example, the feature extractor 120 may extract features from a plurality of constituent pulses forming a waveform of the reference bio-signal. Generally, the bio-signal is a superposition of propagation waves, starting from the heart toward the distal end portions of the body, and reflection waves returning back from the distal end portions. By extracting information on time and/or an amplitude and the like from each of the constituent pulses, and by properly combining the extracted time and amplitude information, the feature extractor 120 may extract features to be used for estimating bio-information. For example, the feature extractor 120 may extract features having a high correlation with bio-information. Further, the feature extractor 120 may perform secondary differentiation on the reference bio-signal, and may extract time and amplitude values of positions with respect to each of the constituent pulses from the differential signal.

However, information which may be extracted from the bio-signal is not limited to time and amplitude information, but may include various types of information. For example, the feature extractor 120 may extract information on a total or partial area under the bio-signal waveform, which may be extracted from the bio-signal.

In response to receipt of a request for calibration from a user or a bio-information estimating apparatus, or in response to predetermined calibration criteria being satisfied, the calibrator 130 may control the sensor 110 to measure a bio-signal to be used for calibration in a reference interval.

Once the feature extractor 120 extracts a reference feature value from a reference bio-signal, the calibrator 130 may determine whether it is suitable to perform calibration based on the reference feature value obtained in the reference interval and an offset value corresponding thereto (or determine whether a condition for performing calibration is satisfied). Specifically, the calibrator 130 may determine whether to perform calibration based on a determination whether the reference feature value and the offset value obtained in the reference interval satisfy a preset condition.

For example, the calibrator 130 may determine whether it is suitable to perform calibration based on the reference feature value. The calibrator 130 may compare the reference feature value with a predetermined feature threshold, and may determine whether it is suitable to perform calibration based on the comparison. In this case, the calibrator 130 may set a feature threshold based on a statistical value of a plurality of feature values obtained from a plurality of users and/or a statistical value of feature values obtained from a specific user when estimating bio-information. For example, the calibrator 130 may determine that it is suitable to perform calibration based on the reference feature value being deviated from the predetermined feature value (or a predetermined feature threshold) by a certain degree or greater, the calibrator 130 may determine that it is not suitable to perform calibration based on the reference feature value.

For example, the calibrator 130 may set a feature threshold by using a predetermined range of values greater or less than a mean value (e.g., a range of values in the top 5% or the bottom 5% with respect to a mean value) of feature values which are extracted for estimating blood pressure for a plurality of users. In an embodiment, the calibrator 130 may set a maximum threshold value (e.g., a value corresponding to the top 5% from the mean value of extracted feature values) and a minimum threshold value (e.g., a value corresponding to the bottom 5% from the mean value of the extracted feature values), and determine that it is suitable to perform calibration based on the reference feature value being smaller than the maximum threshold value and greater than the minimum threshold value. Also, the calibrator 130 may determine that it is not suitable to perform calibration based on the reference feature value being equal to or greater than the maximum threshold value or equal to or smaller than the minimum threshold value.

Alternatively, the calibrator 130 may set a feature threshold by using a predetermined range of values greater or less than a mean value (e.g., a range of values in the top 5% or the bottom 5% with respect to a mean value) of feature values, each of which is extracted for estimating bio-information at a plurality of times for a specific user, or a value which is twice as large as the mean value. In addition, the calibrator 130 may set a feature threshold for a plurality of users at an initial calibration time as described above; and based on estimation of bio-information a predetermined number of times for a specific user, the calibrator 130 may set a feature threshold based on feature values used for estimating bio-information of the specific user.

The above examples are merely given for illustrative purposes and the disclosure is not limited thereto. For example, the calibrator 130 may set a feature threshold by using a probability that the reference feature value is the same or approximate to the mean value of feature values extracted for estimating blood pressure for a plurality of users or extracted for estimating bio-information at a plurality of times for a specific user. The calibrator 130 may determine that it is suitable to perform calibration in response to determining that the reference feature value has a threshold probability or greater of being the same or approximate to the mean value of the extracted feature values, and determine that it is not suitable to perform calibration in response to determining that the reference feature value has a probability less than the threshold probability of being the same or approximate to the mean value of the extracted feature values.

The calibrator 130 may compare the reference feature value with a predetermined feature threshold, and in response to determining that the reference feature value satisfies a predetermined condition based on a result of comparison, the calibrator 130 may determine that it is suitable to perform calibration based on the reference feature value. In the case there are a plurality of reference feature values, and all of the plurality of reference feature values fall within a feature threshold range, the calibrator 130 may determine that the plurality of reference feature values are suitable for calibration. However, the determination is not limited thereto, and in the case where a predetermined number of feature values satisfy a feature threshold range, the calibrator 130 may determine that the feature values are suitable for calibration. Alternatively, the calibrator 130 may combine a plurality of feature values by using a pre-defined combination equation as represented by the following Equation 1, and may compare one combined feature value, obtained as a result of the combination, with a feature threshold, to determine whether the feature value is suitable for calibration.

$$f_{comb} = \frac{f1_{cal}}{f1_{mean}} + \frac{f2_{cal}}{f2_{mean}} \qquad [\text{Equation 1}]$$

Herein, $f_{comb}$ denotes a combined feature value, $f1_{cal}$ and $f2_{cal}$ denote two types of reference features, each of which is obtained in a calibration interval, $f1_{mean}$ and $f2_{mean}$ each denote a mean value of a plurality of feature values f1 and a mean value of a plurality of feature values f2 extracted at a plurality of times of estimating bio-information.

Upon determining that it is suitable to perform calibration, the calibrator 130 may calibrate a bio-information estimation model based on the reference feature value extracted from the reference bio-signal in the reference interval and the offset value corresponding to the reference feature. Here, the offset value may be a measured reference bio-information value, e.g., a reference blood pressure value. The offset value may be measured by a bio-information measuring apparatus, such as a cuff-type blood pressure measuring device, in a reference interval for performing calibration. In an example embodiment, as illustrated in FIG. 3, the offset value may be input by a user by interaction with a user.

For example, by using the reference feature value and the offset value, the calibrator 130 may calibrate a pre-defined bio-information estimation model for estimating bio-information, e.g., a linear function, as represented by the following Equation 2.

$$BP\_est = SF \times \left(\frac{f\_est}{f\_cal} - 1\right) + o\_cal \qquad \text{[Equation 2]}$$

Herein, BP_est denotes an estimated bio-information value, e.g., an estimated blood pressure value, f_est denotes a feature extracted from a bio-signal in a blood pressure estimation interval, f_cal denotes a reference feature extracted in a reference interval, o_cal denotes an offset value corresponding to the reference feature, and SF denotes a pre-defined multiplication coefficient for properly estimating a variation in blood pressure.

The interactor 140 may interact with a user by providing information, receiving a user's request, generating an inquiry (e.g., text including an inquiry sentence) to be given to a user and transmitting the inquiry to the user, receiving a response to the inquiry from the user, and the like. FIG. 3 illustrates a device 30 in which the calibration apparatus 100 is mounted. The interactor 140 may output a user interface (e.g., a graphical user interface (GUI)) including an inquiry. Upon receiving a request for calibration from a user, the interactor 140 may output an inquiry interface for inquiring the user about a reference blood pressure value through a display 32 of the device 30. Further, once the user inputs the reference blood pressure value on the inquiry interface, the interactor 140 may receive and transmit the blood pressure value to the calibrator 130.

Figure 4:
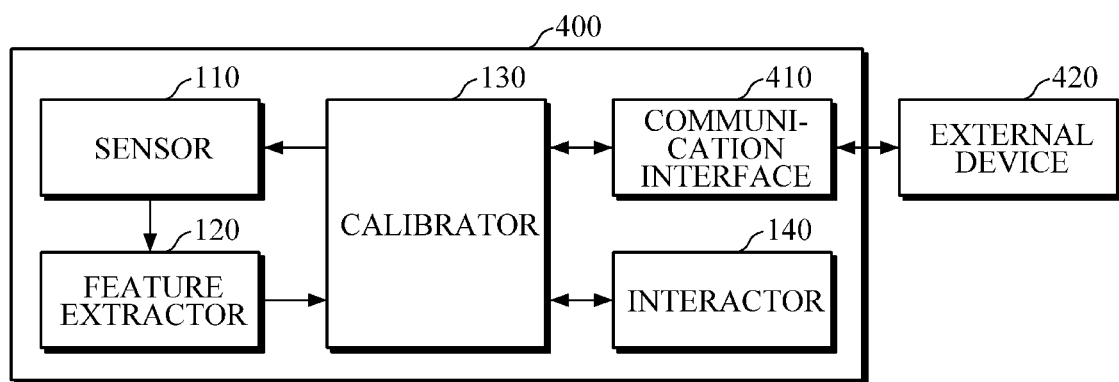
FIG. 4 is a block diagram illustrating a calibration apparatus according to an example embodiment.
Figure 5:
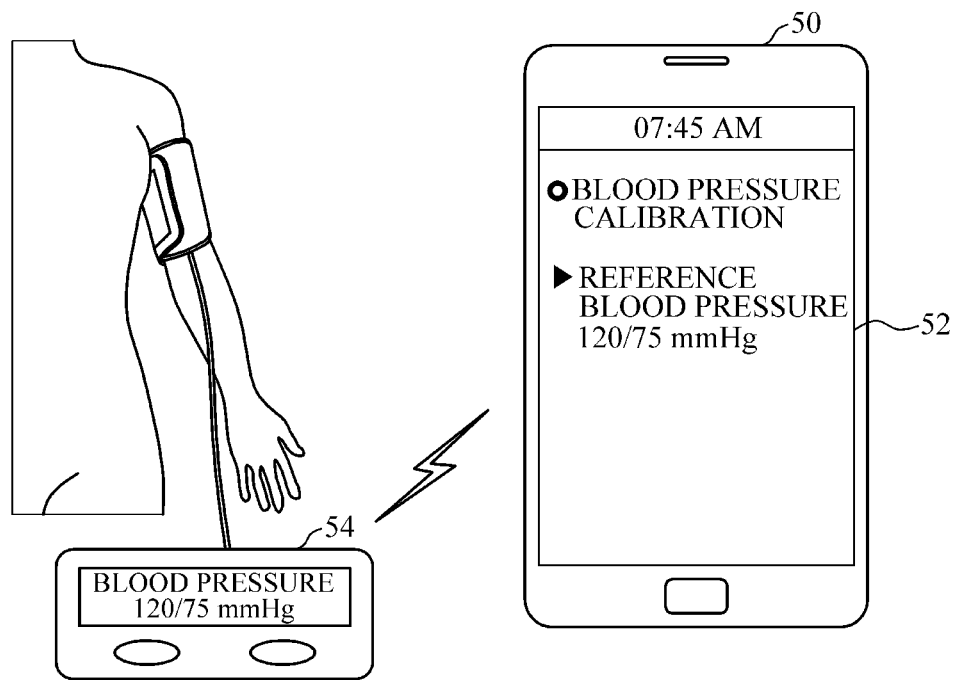
FIG. 5 is a diagram explaining an example of calibration.

FIG. 4 is a block diagram illustrating a calibration apparatus according to an example embodiment. FIG. 5 is a diagram explaining an example of calibration. FIGS. 6A to 6H are diagrams illustrating examples of interaction with a user.

Referring to FIG. 4, the calibration apparatus 400 according to an example embodiment includes a sensor 110, a feature extractor 120, a calibrator 130, an interactor 140, and a communication interface 410. Parts with the same name as those of the calibrating apparatus 100 according to the embodiment of FIG. 1 are described above, such that detailed description thereof will be omitted.

Upon receiving a request for calibration through the interactor 140, the calibrator 130 may control the sensor 110 to measure a reference bio-signal. Further, the calibrator 130 may control the communication interface 410 to communicate with an external device. Particularly, the calibrator 130 may control the communication interface 410 to communicate with an external device for measuring bio-information, and may receive an offset value for calibration from the external device for measuring bio-information through the communication interface 410.

The communication interface 410 may communicate with an external device 420 using communication techniques to transmit and receive various data. In this case, examples of the external device 420 may include a bio-information measuring apparatus such as a cuff-type blood pressure measuring device, a smartphone or a tablet PC that is carried by a user, and the like, but the external device 420 is not limited thereto. Examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, mobile communication, and the like. However, this is merely exemplary and is not intended to be limiting.

FIG. 5 is a diagram illustrating an example in which a device 50, including a calibration apparatus 400, communicates with an external device 54 for measuring blood pressure to receive a reference blood pressure value.

As illustrated in FIG. 5, a user may transmit a request for calibration to the calibration apparatus 400 mounted in the device 50, and may measure a cuff blood pressure using a cuff-type blood pressure measuring device. The user may measure the cuff blood pressure at the same time of transmitting a request for calibration. In this case, while measuring a cuff blood pressure on the left arm, the user may measure a reference bio-signal by touching the sensor 110 with a finger of the right hand. However, it is not necessary to measure the reference blood pressure and the reference bio-signal at the same time.

The interactor 140 may output an offset value, received from the bio-information measuring apparatus through the communication interface 410, to a display 52 of a smart device 50 to provide the offset value to a user as illustrated in FIG. 5.

The calibrator 130 may extract a reference feature from the reference bio-signal, and may determine whether it is suitable to perform calibration based on the received offset value. For example, in response to the received offset value falling within a predetermined range compared to a reference bio-information value previously input by a user, the calibrator 130 may determine that the offset value is suitable for calibration. In this case, the reference bio-information value may be a bio-information value in a normal stable state of a user, e.g., a blood pressure value measured in a resting state before a meal.

In the case where there is no reference bio-information value previously input by a user, the interactor 140 may request a user to input a reference bio-information value, or the calibrator 130 may determine that it is not suitable to perform calibration.

Figure 6A:
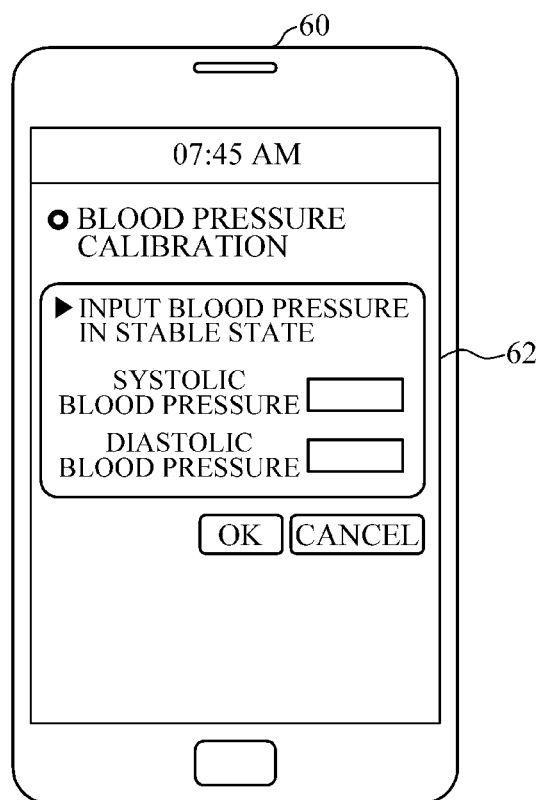
FIGS. 6A to 6H are diagrams illustrating examples of interaction with a user.

In the case where there is a request from the calibrator 130, or there is no pre-stored reference bio-information value, the interactor 140 may request a user to input a reference bio-information value, e.g., a blood pressure value in a stable state, through a display 62 of a device 60 in which a calibration apparatus 400 is mounted, as illustrated in FIG. 6A.

In addition, in an environment where a plurality of offset values may be measured during daily life activities of a user, the calibrator 130 may compare any one offset value that is selected among the plurality of offset values or a statistical value, e.g., a mean value, of the plurality of offset values with an offset value measured in a reference interval for calibration, to determine whether it is suitable to perform calibration.

Figure 6B:
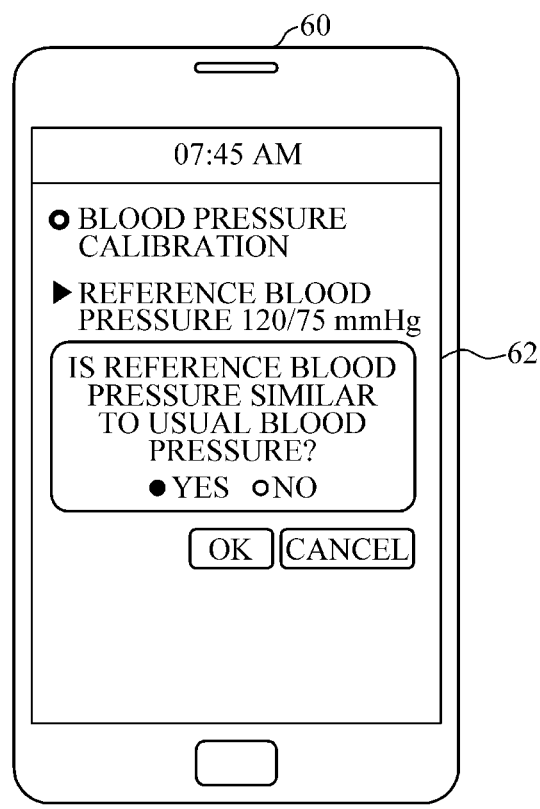

Further, the interactor 140 may inquire a user whether the received offset value is similar to a normal bio-information measurement value of a user, and the calibrator 130 may determine whether it is suitable to perform calibration based on a user's response to the inquiry. For example, as illustrated in FIG. 6B, the interactor 140 may display a reference blood pressure of 125/75 mmHg on the display 62 of the device 60 in which the calibration apparatus 400 is mounted, and may display an inquiry sentence to inquire whether the reference blood pressure value is similar to a normal blood pressure value of a user. Alternatively, the interactor 140 may display a range of values, which are increased or decreased from the reference blood pressure value by a predetermined percentage, and may display an inquiry whether the range of values is similar to a normal blood pressure value.

If a user's response to the inquiry indicating that the reference bio-information value is similar to a normal bio-information value, the calibrator 130 determines that it is suitable to perform calibration; and if not, the calibrator 130 may determine that it is not suitable to perform calibration.

In addition, the calibrator 130 may determine whether a reference feature value and the received offset value are suitable for calibration based on a user's action information.

For example, upon receiving a request for calibration, the interactor 140 may inquire about an action made by a user. In this case, examples of actions made by a user may include actions related to food intake such as before a meal, after a meal, drinking alcohol, caffeine intake, coffee intake, overeating, heavy drinking, and the like or actions related to exercise such strenuous workout, taking a walk, and the like, which may affect normal blood pressure. However, the actions are not limited thereto.

Figure 6C:
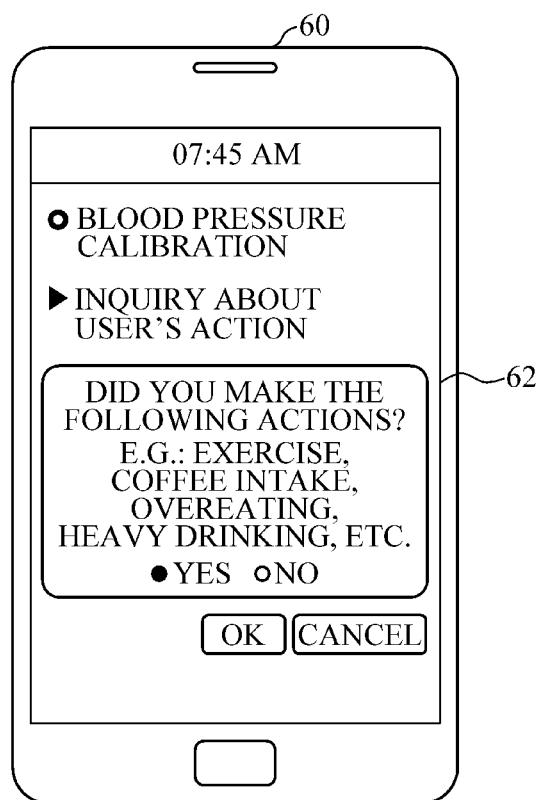

FIG. 6C is a diagram illustrating an example of an inquiry about a user's action, in which the interactor 140 may inquire through the display 62 of the device 60 whether a user makes an action, such as drinking alcohol, caffeine intake, overeating, heavy drinking, and strenuous workout which may negatively affect normal blood pressure, for a predetermine period of time before calibration is to be performed.

In the case where a user's response to the inquiry indicates that the user has made an action which may affect accuracy of calibration, the calibrator 130 may determine that a reference feature value and an offset value are not suitable for calibration.

In addition, upon receiving a request for calibration, the interactor 140 may immediately output guide information for guiding a user to make an appropriate action for calibration for a predetermined period of time. Alternatively, upon determining that a reference feature value and an offset value are not suitable for calibration according to various criteria, the calibrator 130 may output guide information for guiding a user to make an appropriate action for calibration for a predetermined period of time.

Once a predetermined period of time elapses after outputting the guide information, the calibrator 130 may inquire again about a user's action as illustrated in FIG. 6C, or may determine that the user has not made an inappropriate action for a predetermined period of time.

Figure 6D:
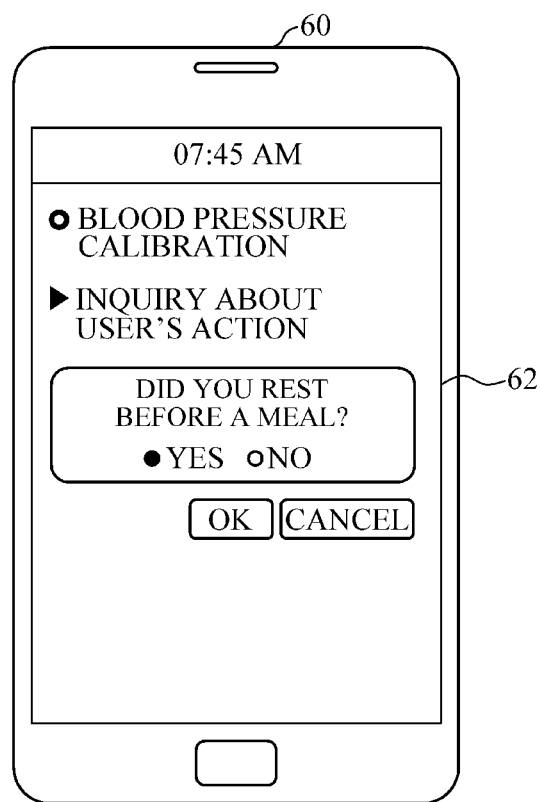

FIG. 6D is a diagram illustrating another example of an inquiry about a user's action, in which upon receiving a request for calibration, the interactor 140 may inquire through the display 62 of the device 60 whether a user has maintained a suitable condition for calibration, such as "did you rest before a meal?", before starting calibration.

Figure 6E:
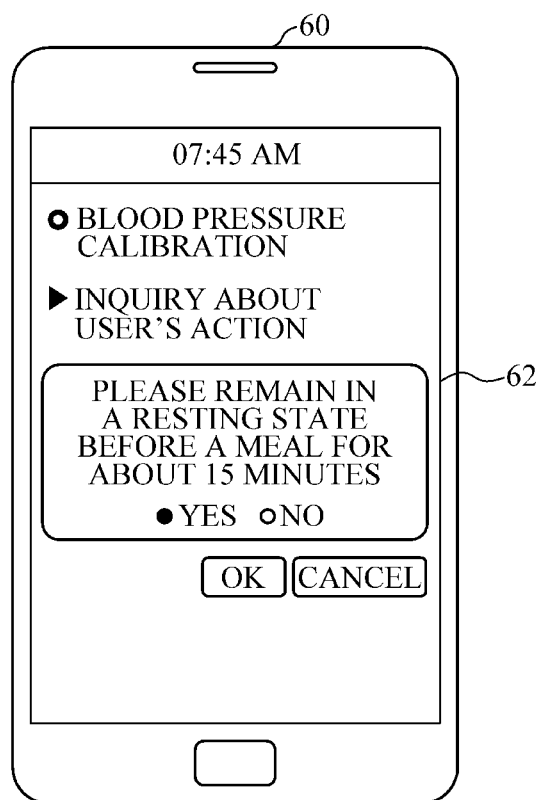

If a user selects "YES" to the inquiry indicating that the user has made an appropriate action for calibration, the calibrator 130 may perform calibration by using the currently obtained reference feature value and offset value. If the user selects "NO" to the inquiry indicating that the user has not made an appropriate action for calibration, the calibrator 140 may determine that it is not suitable to perform calibration. In this case, the interactor 140 may output guide information indicating that a current condition is not suitable for calibration as illustrated in FIG. 6H, or may output guide information regarding an appropriate action for calibration as illustrated in FIG. 6E. Alternatively, the interactor 140 may output the guide information, and at the same time may guide recalibration.

FIG. 6E is a diagram illustrating yet another example of an inquiry to a user, in which upon receiving a request for calibration, the interactor 140 may output guide information immediately before starting calibration to guide a user to make an appropriate action for calibration for a predetermined period of time.

For example, upon receiving a request for calibration, the interactor 140 may output information such as "please remain in a resting state before a meal for about 15 minutes" as illustrated in FIG. 6E, and may guide a user to rest on an empty stomach for a predetermined period of time. In this case, along with the guide information for guiding a user to rest before a meal, the interactor 140 may output information indicating that calibration will be started shortly after a lapse of a predetermined period of time, or information for guiding a user to request calibration again after a lapse of a predetermined period of time. Further, the calibrator 130 may combine two or more reference features, offset values, and user actions to determine whether it is suitable to perform calibration. For example, the calibrator 130 may first inquire about a user's action, and if a response to the inquiry indicates that the user has not made an inappropriate action, the calibrator 130 may then determine whether it is suitable to perform calibration using a reference feature and/or an offset value.

Upon determining that it is suitable to perform calibration using the reference feature value extracted in the current reference interval and the offset value, the calibrator 130 may calibrate a bio-information estimation model by using the reference feature value and the offset value.

Figure 6F:
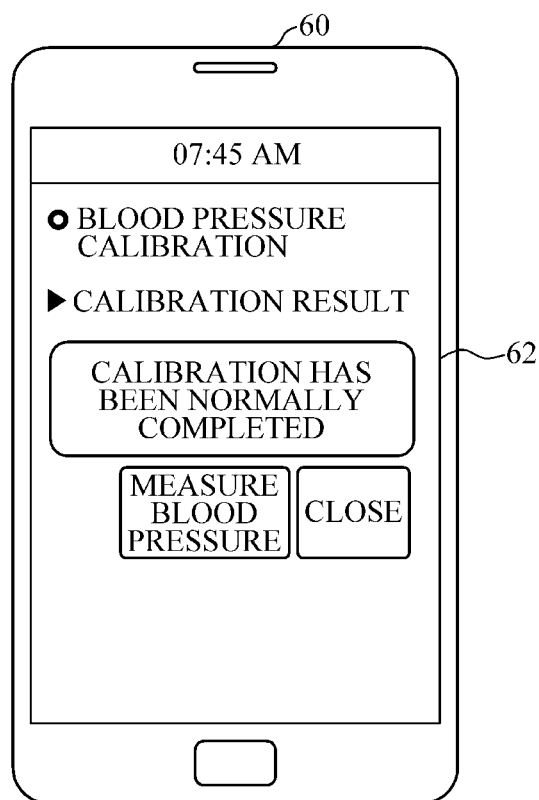

FIG. 6F is a diagram illustrating an example of guide information displayed after calibration is completed, indicating that calibration has been normally completed. As illustrated in FIG. 6F, once calibration has been normally completed, the interactor 140 may output information such as "calibration has been normally completed." In the case where the device 60 has a function of measuring bio-information, the interactor 140 may output an object inquiring whether to continue measuring bio-information (e.g., measuring blood pressure) by using the calibrated bio-information estimation model.

Figure 6G:
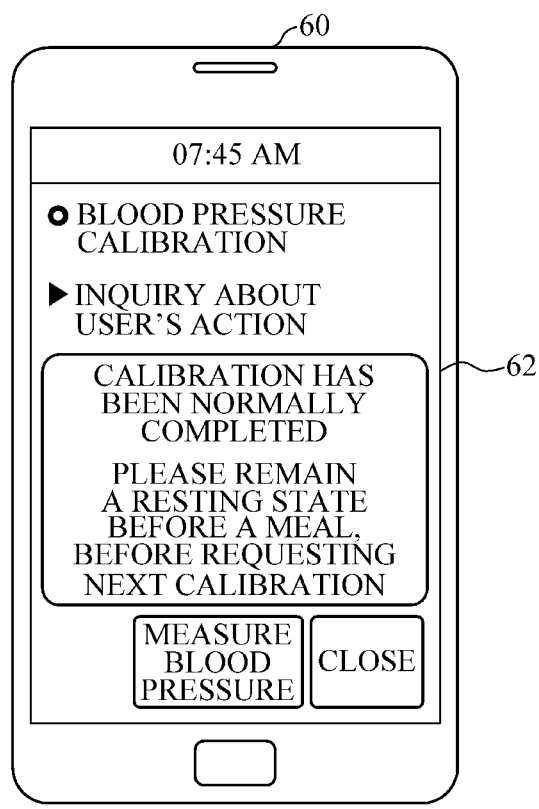
Figure 6H:
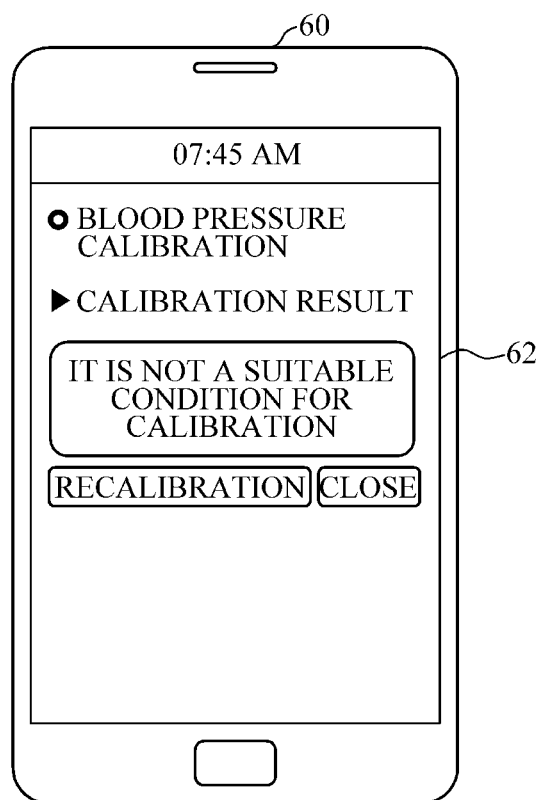

FIG. 6G is a diagram illustrating guide information, displayed after calibration is completed, indicating an appropriate action to be made by a user for calibration before the user requests next calibration. As illustrated in FIG. 6G, once calibration is normally completed, the interactor 140 may output information, such as "please remain in a resting state before a meal, before requesting next calibration," alone or in combination with information indicating that calibration is normally completed.

In addition, once the calibrator 130 determines that it is not a suitable to perform calibration, the interactor 140 may output information through the display 62 of the device 60 that it is not a suitable condition for calibration as illustrated in FIG. 6H. Additionally or alternatively, as illustrated in FIG. 6H, the interactor 140 may output an object (e.g., "re-calibration" button) inquiring whether to perform calibration again.

Figure 7:
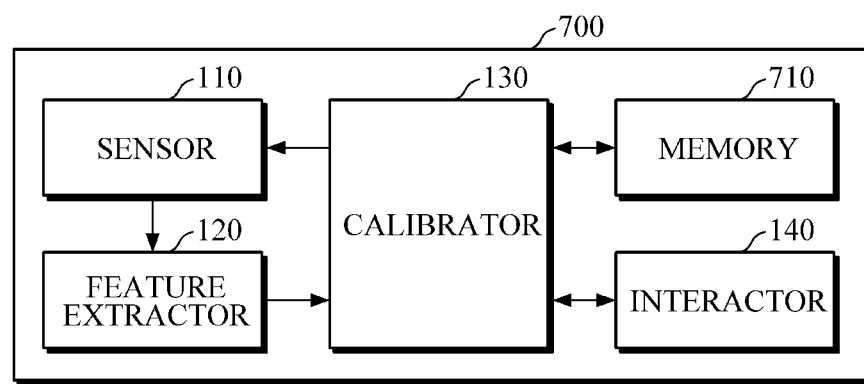
FIG. 7 is a block diagram illustrating a calibration apparatus according to an example embodiment.
Figure 8A:
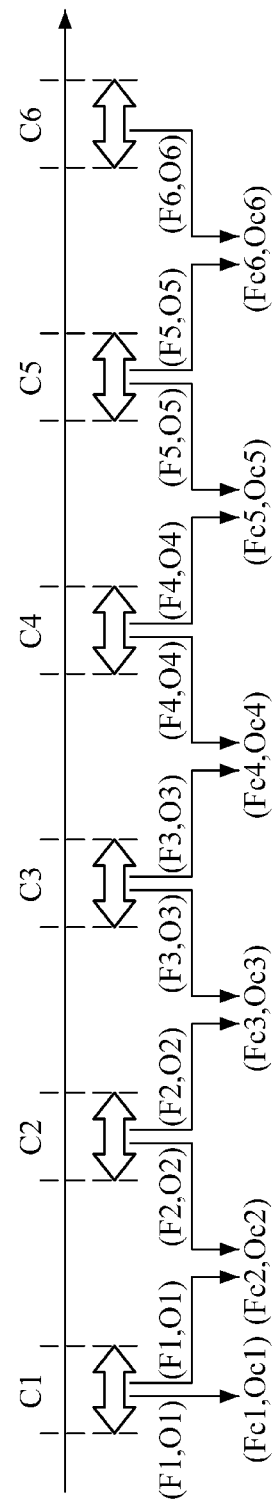
FIGS. 8A and 8B are diagrams explaining a calibration process according to an example embodiment.
Figure 8B:
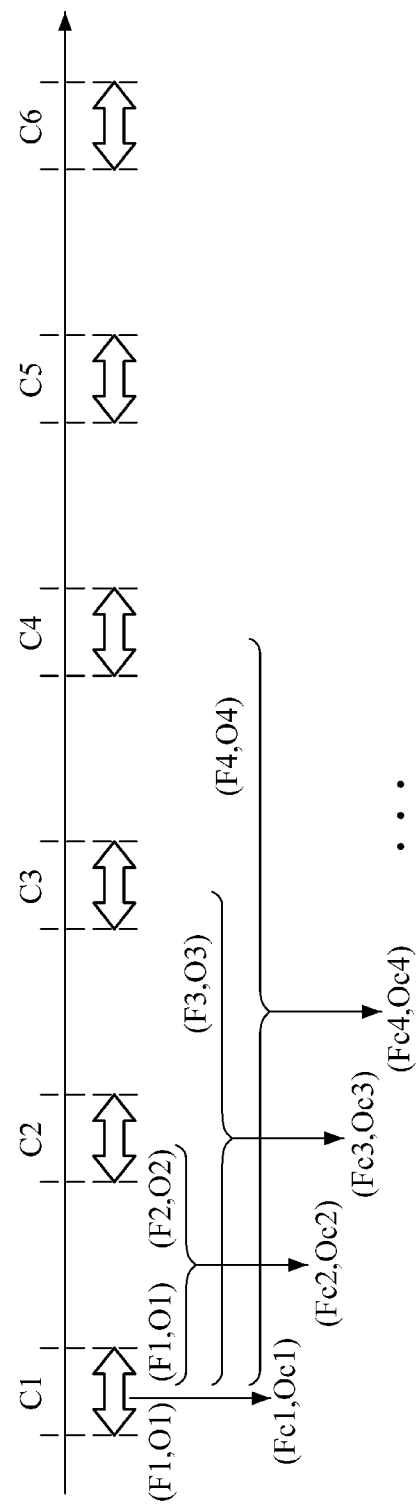

FIG. 7 is a block diagram illustrating a calibration apparatus according to an example embodiment. FIGS. 8A and 8B are diagrams explaining a calibration process according to an example embodiment.

Referring to FIG. 7, the calibration apparatus 700 includes a sensor 110, a feature extractor 120, a calibrator 130, an interactor 140, and a memory 710. The same elements as those of the bio-information measuring apparatuses 100 and 400 described above will be briefly described below.

According to an example embodiment, the calibration apparatus 700 may perform multi-calibration based on a set of a plurality of reference feature values and offset values which are obtained in each reference interval for performing a plurality of calibrations. That is, when performing calibration in a first reference interval, the calibration apparatus 700 may calibrate a bio-information estimation model based on a set of a plurality of reference feature values and offset values obtained in the first reference interval through a second reference interval that precedes the first reference interval.

For example, as illustrated in FIG. 8A, the calibration apparatus 700 may perform N-point multi calibration, in which N is a predetermined number. In this case, the first reference interval is an interval in which calibration is currently performed, and the second reference interval may be a previous reference interval which is an (N−1)th interval from the first reference interval. In another example, the calibration apparatus 700 may perform accumulated multi-calibration. In this case, the first reference interval may be a reference interval in which calibration is currently performed, and the second reference interval may be an initial reference interval. However, the example embodiments are not limited thereto and may vary according to circumstances.

Referring to FIG. 8A, an example of a two-point multi-calibration with N being set to 2.

It is assumed that a reference interval C1 at a time when initial calibration is performed is a first reference interval. The sensor 110 measures a reference bio-signal in the reference interval C1, and the feature extractor 120 extracts a reference feature value F1 from the reference bio-signal. Upon obtaining an offset value 01, corresponding to the reference feature value F1, from an external device or a user, the calibrator 130 determines whether it is suitable to perform calibration based on a first reference set (F1, 01) including the reference feature value F1 and the offset value 01 corresponding to the reference interval C1. Upon determining that it is suitable to perform calibration, the calibrator 130 may store the first reference set (F1, 01) in the memory 710. Further, since the reference interval C1 is the first reference interval, and there is no second reference interval that precedes the reference interval C1, the calibrator 130 may generate a first calibration set (Fc1, Oc1) for calibration based on only the first reference set (F1, 01), and may perform calibration by using only the generated first calibration set (Fc1, Oc1).

Likewise, when it is assumed that a reference interval C2 is a first reference interval for performing second calibration, the first reference interval C1, which is an (N−1)th previous reference interval (that is, (2−1)th previous reference interval), becomes a second reference interval. If it is determined that a second reference set (F2, 02) including a reference feature value F2 and an offset value 02, obtained in the reference interval C2, is suitable for calibration, the calibrator 130 may store the second reference set (F2, 02) in the memory 710, and may generate a second calibration set (Fc2, Oc2) for calibration based on the first reference set (F1, 01) and the second reference set (F2, 02). In addition, the calibrator 130 may perform calibration by using the second calibration set (Fc2, Oc2).

For example, the calibrator 130 may obtain a reference feature value and an offset value for calibration by applying pre-defined various linear or non-linear functions to N number of reference feature values and N number of offset values.

For example, the calibrator 130 may calculate a mean value of the N number of reference feature values and a mean value of the N number of offset values by using an equation for calculating a mean value as represented by the following Equation 3, and may obtain each of the calculated mean values as a reference feature value and an offset value of a calibration set.

$$F_{ci} = \frac{F_{i-(N-1)} + \ldots + F_i}{N}$$ [Equation 3]

$$O_{ci} = \frac{O_{i-(N-1)} + \ldots + O_i}{N}$$

Herein, $F_{ci}$ denotes a reference feature value for calibration in an i-th reference interval; Fi denotes an i-th reference feature value; $O_{ci}$ denotes an offset value for calibration in the i-th reference interval; Oi denotes an i-th offset value; N is a predetermined integer greater than or equal to 2; and i denotes an integer greater than or equal to N. In this case, in a reference interval with i being smaller than N, the calibrator 130 may obtain a mean value of the first to the i-th reference feature values and a mean value of the offset values as the reference feature value and the offset value for calibration in the i-th reference interval.

In another example, the calibrator 130 may multiply each reference feature value and each offset value by a weighted value to calculate a weighted average of each of the values as represented by the following Equation 4, and may obtain each of the calculated weighted average values as a reference feature value and an offset value of a calibration set.

$$F_{ci} = \frac{w_{i-(N-1)} F_{i-(N-1)} + \ldots + w_i F_i}{w_{i-(N-1)} + \ldots + w_i}$$ [Equation 4]

$$O_{ci} = \frac{w_{i-(N-1)} O_{i-(N-1)} + \ldots + w_i O_i}{w_{i-(N-1)} + \ldots + w_i}$$

Herein, $F_{ci}$ denotes a reference feature value for calibration in an i-th reference interval; Fi denotes an i-th reference feature value obtained in the i-th reference interval; $O_{ci}$ denotes an offset value for calibration in the i-th reference interval; Oi denotes an i-th offset value obtained in the i-th reference interval; N is a predetermined integer greater than or equal to 2; and i denotes an integer greater than or equal to N. $W_i$ denotes a weighted value, which may be set differently for the reference feature value and the offset value. In this case, in a reference interval with i being smaller than N, the calibrator 130 may obtain a weighted average value of the first to the i-th reference feature values and a weighted average value of the offset values as the reference feature value and the offset value for calibration in the i-th reference interval.

Further, a weighted value corresponding to each reference interval may be set based on reliability of the reference feature value or the offset feature obtained in each reference interval. For example, in the case where a reference blood pressure value, which is obtained in the i-th reference interval, has a high reliability as the value is close to an actual blood pressure value or a mean blood pressure value, a weighted value may be set to a high value. Alternatively, in the case where a user makes an action, which negatively affects blood pressure, in the i-th reference interval, an i-th weighed value may be set to a relatively low value.

In another example, a functional equation for obtaining a reference feature value and an offset value of a calibration set may be defined as a non-linear function as represented by the following Equation 5, and different equations may be set for each of the reference feature value and the offset value.

$$F_{ci} = \frac{1}{F_m}, F_m = \frac{\left(\frac{1}{F_{i-(N-1)}} + \ldots + \frac{1}{F_i}\right)}{N}$$

$$O_{ci} = \frac{O_{i-(N-1)} + \ldots + O_i}{N}$$

[Equation 5]

Herein, $F_{ci}$ denotes a reference feature value for calibration in an i-th reference interval; Fi denotes an i-th reference feature value obtained in the i-th reference interval; $O_{ci}$ denotes an offset value for calibration in the i-th reference interval; and Oi denotes an i-th offset value obtained in the i-th reference interval. In this case, N is a predetermined integer greater than or equal to 2; and i denotes an integer greater than or equal to N. In a reference interval with i being smaller than N, the calibrator 130 may obtain the reference feature value and the offset value for calibration by using only the first to the i-th reference feature values and the offset values.

As illustrated in FIG. 8A, the above processes may be repeated while a current reference interval is changed from C1 to C6. As described above, the N-point multi calibration is performed in such a manner that a new calibration set of a reference feature value and an offset value is generated by using reference feature values and offset values obtained in a total of N number of previous reference intervals, and calibration is performed by using the generated calibration set of the reference feature value and the offset value.

Referring to FIG. 8B, an example of a method of performing accumulated multi-calibration will be described below. In this case, it is assumed that a first reference interval is a reference interval in which calibration is currently performed, and a second reference interval is an initial reference interval C1.

In a manner similar to FIG. 8A, determination is made as to whether it is suitable to perform calibration based on sets (F1, O1), (F2, O2), (F3, O3), and (F4, O4) of reference feature values and offset values, which are obtained in reference intervals from the first reference interval C1 to a fourth reference interval C4, and the sets of values are in the memory 710.

Assuming that a current reference interval is the first reference interval C1, a first calibration set (Fc1, Oc1) may be obtained based on a first reference set (F1, O1) obtained in the first reference interval C1. Assuming that the current reference interval is now a second reference interval C2, a second calibration set (Fc2, Oc2) may be obtained based on the first reference set (F1, O1) of the first reference interval C1 and a second reference set (F2, O2) of the current reference interval C2. Likewise, assuming that a current reference interval is now a third reference interval C3, a third calibration set (Fc3, Fc4) may be generated based on the first reference set (F1, O1), the second reference set (F2, O2), and a third reference set (F3, O3) by accumulating the sets of the reference feature values and offset values corresponding to the first reference interval (the third reference interval C3) through the second reference interval (the first reference interval C1), that is, accumulating the sets corresponding to the third reference interval C3, the second reference interval C2, and the first reference value C1. In this case, a function for generating a calibration set may be pre-defined as described above.

In the example embodiments, by performing current calibration using a plurality of reference feature values and offset values, which are determined to be suitable for calibration, in a plurality of calibration intervals, a bio-information estimation model may be calibrated more accurately.

The memory 710 may store various types of reference information to be used for calibration, and reference bio-signals, reference feature values, offset values, and the like which are obtained for performing calibration. In this case, the reference information may include a user's age, sex, health condition, reference bio-information measured in a stable state, basic template information for interaction, a bio-information estimation model, and the like. In this case, the memory 710 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Figure 9:
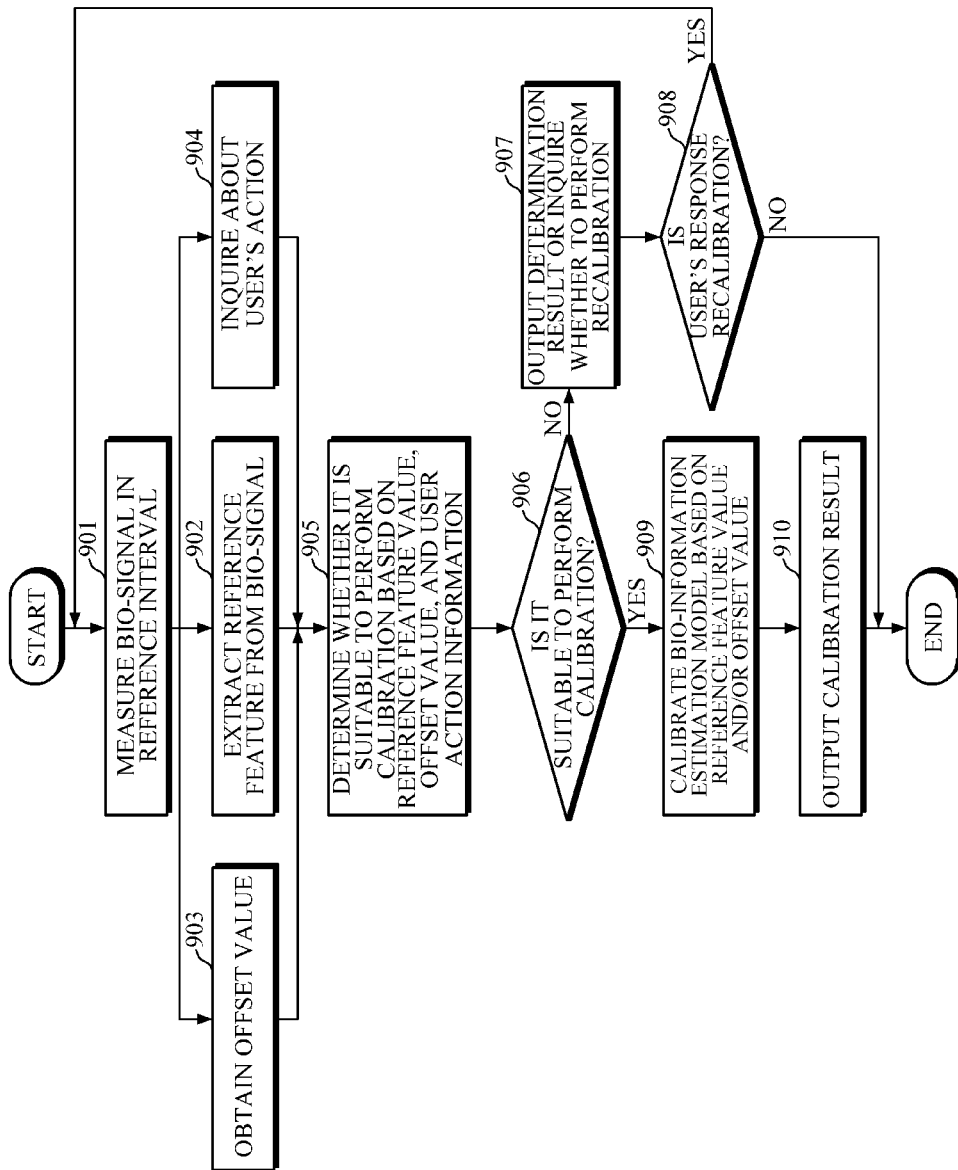
FIG. 9 is a flowchart illustrating a calibration method according to an example embodiment.

FIG. 9 is a flowchart illustrating a calibration method according to an example embodiment.

The calibration method of FIG. 9 is an example of a calibration method performed by any one of the calibration apparatuses 100, 400, and 700 described above.

In response to a request for calibration, the calibration apparatus may measure a bio-signal in a reference interval in 901. In an example embodiment, the bio-signal may be a photoplethysmogram (PPG) signal, but is not limited thereto.

Then, the calibration apparatus may extract reference features from the reference bio-signal measured in the reference interval in 902. For example, the calibration apparatus may obtain, from the bio-signal, one or more constituent pulses forming a waveform of the bio-signal, and may extract features based on time and amplitude values of positions with respect to each of the constituent pulses. In this case, the constituent pulses may be obtained by using a differential signal, which is obtained by performing second differentiation on the bio-signal.

Further, the calibration apparatus may obtain offset values for calibration which correspond to the reference feature values in 903. The offset value may be a measured bio-information value, which is measured by the bio-information measuring apparatus at the same time when measuring the reference bio-signal or within a predetermined period of time before and/or after measuring the reference bio-signal, or may be input by a user or may be received by communication with the bio-information measuring apparatus.

Subsequently, the calibration apparatus may inquire about an action made by a user in a reference interval for performing calibration, or within a predetermined period of time before and/or after the reference interval, and may receive a user's response to the inquiry in 904. In this case, examples of the inquiry may include smoking, strenuous exercise, overeating, heavy drinking, and the like, which may affect bio-information values such as a blood pressure value. However, operation 904 may be omitted depending on an embodiment.

Next, the calibration apparatus may determine whether the reference feature value obtained in the reference interval and the offset value are suitable for calibration based on one or more of the reference feature value, the offset value, and user action information in 905. The example embodiments of determining whether the reference feature value and the offset value are suitable for calibration has been described above in detail, such that description thereof will be omitted.

Then, upon determining in 906 that the values are not suitable for calibration, the calibration apparatus may output a determination result for a user, or may inquire a user whether to perform recalibration in 907.

Subsequently, if a user's response indicates recalibration in 908, the calibrating apparatus may return to operation 901 to measure a bio-signal by setting a predetermined time interval after a current time or after a lapse of a predetermined time as a reference interval.

Upon determining that the values are suitable for calibration in 906, the calibration apparatus may calibrate a bio-information estimation model based on the reference feature value and the offset value in 909. In this case, the calibration apparatus may perform single calibration by using only the reference feature value and the offset value which are measured in the current reference interval, or may perform multi-calibration by using the reference feature values and the offset values which are obtained in two or more reference intervals including a previous reference interval and the current reference interval.

Next, the calibration apparatus may output a calibration result in 910.

Figure 10:
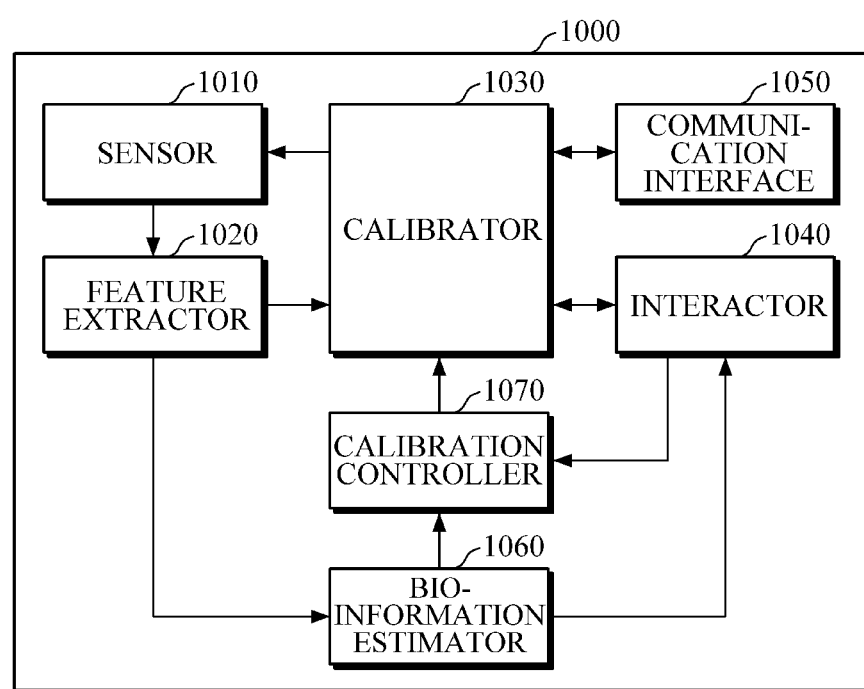
FIG. 10 is a block diagram illustrating a bio-information estimating apparatus according to an example embodiment.

FIG. 10 is a block diagram illustrating a bio-information estimating apparatus according to an example embodiment.

One or more of the calibration apparatuses 100, 400, and 700 according to various embodiments described above may be included in the bio-information estimating apparatus 1000. Various embodiments of the bio-information measuring apparatus which will be described below may be embedded in various devices such as a portable wearable device, a smart device, and the like. Examples of the various devices may include: a wearable device manufactured in various types such as a smart watch, a smart band-type device, a headphone-type device, a headband-type device, and the like; and a mobile device such as a smartphone, a tablet PC, and the like, but the devices are not limited thereto.

Referring to FIG. 10, the bio-information estimating apparatus 1000 includes a sensor 1010, a feature extractor 1020, a calibrator 1030, an interactor 1040, a communication interface 1050, a bio-information estimator 1060, and a calibration controller 1070. In this case, the feature extractor 1020, the calibrator 1030, the interactor 1040, the bio-information estimator 1060, and the calibration controller 1070 may be included in one or more processors. Repetitive description of the parts that correspond to the elements described above will be omitted.

In response to a request for calibration or a request for estimating bio-information, the sensor 1010 may measure a bio-signal from an object. In this case, the bio-signal may be a photoplethysmogram (PPG) signal. Further, the sensor 1010 may include a pulse wave sensor including: one or more light sources which emit light onto an object; and one or more detectors which detect light reflected from the object. The one or more light sources may emit light of multiple wavelengths, and may be positioned at different distances from the detectors.

The feature extractor 1020 may extract features from the bio-signal measured by the sensor 1010.

In response to a request for calibration, the calibrator 1030 may perform calibration based on a reference feature, which are extracted from the reference bio-signal measured in a reference interval, and an offset value corresponding thereto. As described above, the calibrator 1030 may determine whether it is suitable to perform calibration based on one or more of the reference feature, the offset value, and user action information, and upon determining that it is suitable to perform calibration, the calibrator 1030 may calibrate a bio-information estimation model.

The interactor 1040 may interact with a user to receive various types of information from the user, and may transmit the received information to the calibrator 1030 and the calibration controller 1070. For example, while performing calibration in response to a request of the calibrator 1030, the interactor 1040 may inquire a user about relevant information, and may transmit a user's response to the inquiry to the calibrator 1030. Further, upon receiving a request for calibration from a user, the interactor 1040 may transmit the calibration request to the calibration controller 1070. In addition, upon obtaining a bio-information estimation result form the bio-information estimator 1060, the interactor 1040 may output the bio-information estimation result and may provide the result to a user.

The communication interface 1050 may communicate with various external devices to transmit and receive various types of data. For example, in response to a request for calibration, the communication interface 1050 may receive an offset value from an external device, and may transmit the offset value to the calibrator 1030. Further, the communication interface 1050 may transmit a calibration result, a bio-information estimation result, and the like to an external device, so that the external device may perform an additional operation.

In response to a request for estimating bio-information, once an estimated feature is extracted based on an estimated bio-signal which is measured in a bio-information estimation interval, the bio-information estimator 1060 may estimate bio-information by using the extracted estimated feature. For example, an bio-information estimation model may be calibrated by the calibrator 1030 by using the above Equation 2, and the bio-information estimator 1060 may estimate bio-information by substituting the extracted feature value by using the calibrated bio-information estimation model.

In addition, once the calibrator 1030 performs a plurality of calibrations, the bio-information estimator 1060 may obtain a final bio-information measurement value in a current estimation interval by using a plurality of calibrated bio-information estimation models. For example, in the case where the calibrator 1030 calibrates a blood pressure estimation model three times in total before a current time of estimating blood pressure, to generate a first estimation model, a second calibration model, and a third calibration model, the bio-information estimator 1060 may substitute the extracted feature, which is extracted in the current estimation interval, by using the first estimation model to obtain a first blood pressure value, substitute the extracted feature by using the second estimation model to obtain a second blood pressure value, and substitute the extracted feature by using the third estimation model to obtain a third blood pressure value. Further, the first blood pressure value, the second blood pressure value, and the third blood pressure value may be linearly combined (e.g., average) to obtain a final blood pressure value.

The bio-information estimator 1060 may determine a previously calibrated bio-information estimation model for use in estimating bio-information according to predetermined criteria. For example, the bio-information estimator 1060 may determine a bio-information estimation model at predetermined intervals (e.g., 12 hours, day, week, month, etc.). That is, if the predetermined interval is a "day", the bio-information estimator 1060 may use all the bio-information estimation models which are calibrated during the day, on which a current time of estimating bio-information falls. In another example, the bio-information estimator 1060 may use a bio-information estimation model which is calibrated at a time close to the current time of estimating bio-information during a predetermined period of time (e.g., week, month, etc.). For example, in the case where a predetermined period of time is a "week," and a current time of estimating bio-information is "10 am. on Sunday," the bio-information estimator 1060 may use bio-information estimation models calibrated at 9 am. from Monday to Sunday during the week.

The calibration controller 1070 may control the calibrator 1030 based on a user's request, reference information, and the like. For example, upon receiving a request for calibration from a user through the interactor 1040, the calibration controller 1070 may control the calibrator 1030 to request calibration of a bio-information estimation model. Further, in the case where reference information, such as a calibration interval, is predetermined, the calibration controller 1070 may control the calibrator 1030 automatically at the predetermined calibration interval.

In addition, the calibration controller 1070 may determine whether to perform recalibration based on a bio-information estimation result, and may control the calibrator 1030 based on the determination. For example, based on a user's response to a bio-information estimation result, the calibration controller 1070 may determine whether to perform recalibration. For example, while outputting a bio-information estimation result to a user, the interactor 1040 may inquire the user whether there is abnormality in the bio-information estimation result, and may transmit a user's response to the inquiry to the calibration controller 1070. In another example, in response to a bio-information estimation result not satisfying predetermined criteria, the calibration controller 1070 may determine to perform recalibration. In this case, reference information including a user's normal blood pressure range, an accumulated number of times of abnormality, and the like may be predetermined. In the case where a total number of times an estimated blood pressure value falls outside a normal blood pressure range satisfies an accumulated number of times of abnormality, the calibration controller 1070 may determine to perform recalibration. However, the determination is not limited thereto.

Figure 11:
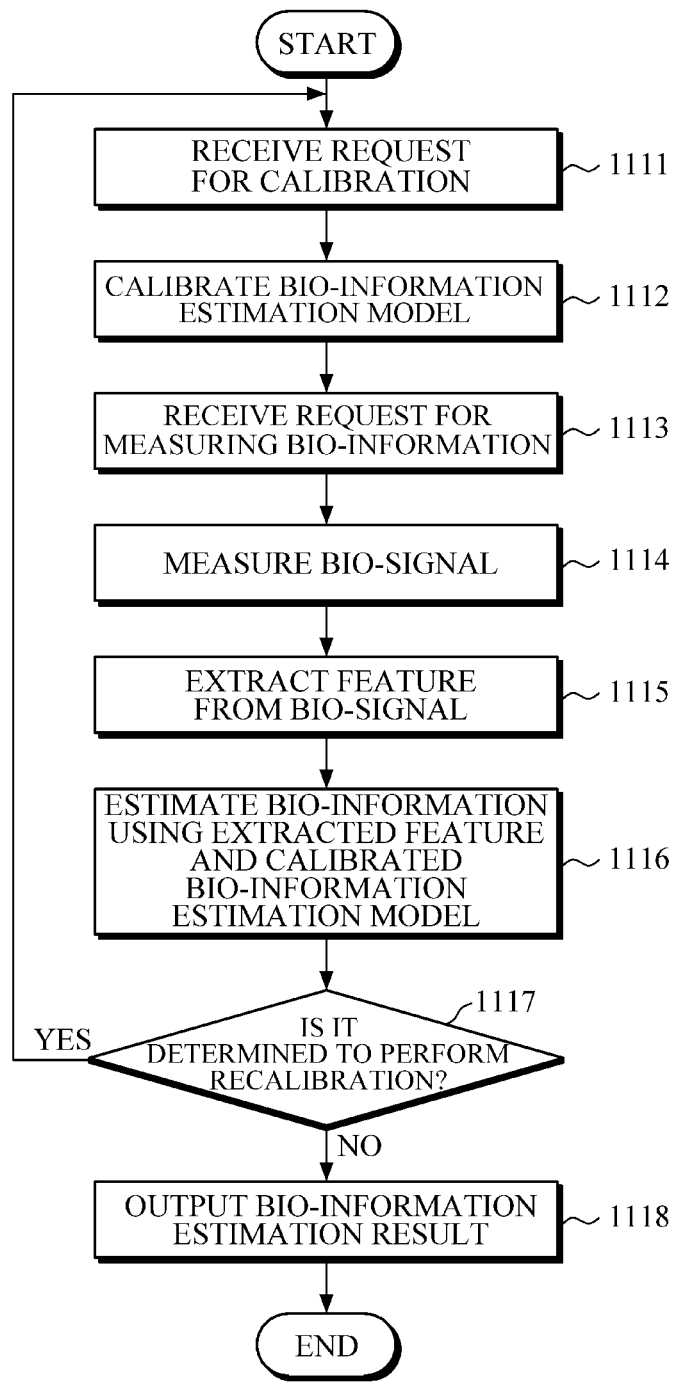
FIG. 11 is a flowchart illustrating a bio-information estimating method according to an example embodiment.

FIG. 11 is a flowchart illustrating a bio-information estimating method according to an example embodiment.

The bio-information estimating method of FIG. 11 may be an example of a bio-information estimating method performed by the bio-information estimating apparatus 1000 of FIG. 10.

The bio-information estimating apparatus 1000 may receive a request for calibration in 1111. The request for calibration may be input by a user, or may be generated at predetermined calibration intervals.

The bio-information estimating apparatus 1000 may calibrate a bio-information estimation model in 1112 in a reference interval for performing calibration. The bio-information estimating apparatus 1000 may determine whether it is suitable to perform calibration based on one or more of a reference feature value extracted from a bio-signal in the reference interval, an offset value corresponding to the reference feature value, and user action information. Upon determining that it is suitable to perform calibration, the bio-information estimating apparatus 1000 may calibrate a bio-information estimation model based on the reference feature value and the offset value. Operations 1111 and 1112 may be performed a plurality number of times during a predetermined period of time.

Subsequently, the bio-information estimating apparatus 1000 may receive a request for measuring bio-information in 1113. The request for measuring bio-information may be input by a user, or may be generated automatically at predetermined calibration intervals.

Next, the bio-information estimating apparatus 1000 may measure a bio-signal from an object in 1114. The bio-signal may be a photoplethysmogram (PPG) signal, and may be measured for a predetermined period of time by a pulse wave sensor including one or more light sources and one or more detectors.

Then, the bio-information estimating apparatus 1000 may extract features for estimating bio-information in 1115 from the bio-signal measured in 1114. The features may be obtained from values such as time and amplitude values obtained at one or more positions of the bio-signal, and/or a total or partial area under a bio-signal waveform, or a combination of these values. For example, the bio-information estimating apparatus 1000 may perform second differentiation on the bio-signal, and may extract a time value at a local minimum point of the differential signal, and an amplitude value corresponding to the time value. In this case, the local minimum point may indicate concave portions of a waveform of the second differential signal.

Subsequently, the bio-information estimating apparatus 1000 may estimate bio-information in 1116 by using the extracted features and the bio-information estimation model calibrated in 1112. For example, if a bio-information estimation model, defined by Equation 2, is calibrated, the bio-information estimating apparatus 1000 may estimate bio-information by inputting the extracted features in the calibrated bio-information estimation model.

Next, the bio-information estimation apparatus 1000 may determine whether to perform recalibration based on a bio-information estimation result in 1117.

Then, upon determining to perform recalibration in 1117, the bio-information estimation apparatus 1000 may return to operation 1111. Upon determining not to perform recalibration, the bio-information estimating apparatus 1000 may output a bio-information estimation result in 1118. The bio-information estimation result may be visually output to a display, or may be output in various other means, e.g., through voice. In this case, if a bio-information estimation result falls outside a normal range, the bio-information estimating apparatus 1000 may output warning information along with the estimation result. The warning information may be output in a manner that visually distinguishes the warning information from a normal estimation result. For example, if an estimation result is normal, the estimation result may be output in green, and if abnormal, the estimation result may be output in red. Alternatively, while visually outputting an estimation result, the bio-information estimating apparatus may warn a user of an abnormal estimation result through vibrations or tactile sensation using a haptic device. However, these are merely examples and a method of outputting the warning information is not limited thereto.

The example embodiments may be provided as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments for implementing the disclosure can be easily deduced by one of ordinary skill in the art.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing steps may employ any number of related art techniques for electronics configuration, signal processing and/or control, data processing and the like.

While a few example embodiments have been described above, the scope of the disclosure is not limited thereto and various modifications and improvements made by those of ordinary skill in the art to concepts defined in the following claims should be understood to fall within the scope of the disclosure.

What is claimed is:

1. An electronic device for estimating a bio-information, the electronic device comprising:

a sensor configured to obtain a bio-signal from an object in a reference interval; and a processor configured to:

receive an offset value measured from the object in the reference interval;

compare the offset value with a reference bio-information value;

in response to the offset value falling within a predetermined range compared to the reference bio-information value, determine that a condition is satisfied; and calibrate a bio-information estimation model based on the offset value and a reference feature value, based on determining that the condition is satisfied, and not calibrate the bio-information estimation model, based on determining that the condition is not satisfied.

2. The electronic device of claim 1, wherein the processor further configured to receive the reference bio-information value from a user.

3. The electronic device of claim 1, wherein the processor further configured to output an inquiry to a user and receive a response to the inquiry from the user.

4. The electronic device of claim 3, wherein the processor is further configured to output the inquiry relating to an action made by the object during a predetermined period of time prior to the reference interval.

5. The electronic device of claim 3, wherein the processor is further configured to determine whether the condition is satisfied based on the response to the inquiry.

6. The electronic device of claim 1, wherein the processor is further configured to output information about an action to be made by the object during a predetermined period of time prior to performing calibration of the bio-information estimation model.

7. The electronic device of claim 6, wherein the action to be made by the object comprises having a resting state before a meal.

8. The electronic device of claim 1, wherein the processor is further configured to, based on determining that the condition is not satisfied, guide the object to request recalibration, and/or to provide information indicating that calibration is not to be performed.

9. The electronic device of claim 1, further comprising a communication interface configured to receive the offset value from an external device.

10. The electronic device of claim 1, wherein the processor is further configured to receive the offset value from a user.

11. The electronic device of claim 1, wherein the processor is further configured to estimate the bio-information based on the calibrated bio-information estimation model and a feature value extracted from the bio-signal in a bio-information estimation interval.

12. A method of estimating a bio-information, the method comprising:

obtaining a bio-signal from an object in a reference interval;

receiving an offset value measured from the object in the reference interval;

comparing the offset value with a reference bio-information value;

in response to the offset value falling within a predetermined range compared to the reference bio-information value, determining that a condition is satisfied; and calibrating a bio-information estimation model based on the offset value and a reference feature value, based on determining that the condition is satisfied, and not calibrating the bio-information estimation model, based on determining that the condition is not satisfied.

13. The method of claim 12, further comprising:
receiving the reference bio-information value from a user.

14. The method of claim 12, further comprising outputting, through an interface, an inquiry to a user and receiving a response to the inquiry from the user.

15. The method of claim 12, further comprising outputting an inquiry about an action made by the object during a predetermined period of time prior to the reference interval,
wherein the determining whether the condition is satisfied comprises determining whether the condition is satisfied based on a response to the inquiry.

16. The method of claim 12, further comprising, based on determining that the condition is not satisfied, guiding the object to request recalibration, and/or providing information indicating that calibration is not to be performed.

17. The method of claim 12, further comprising receiving the offset value corresponding to the reference interval from at least one of an external device and a user.

18. The method of claim 12, further comprising estimating the bio-information based on the calibrated bio-information estimation model and a feature value extracted from the bio-signal in a bio-information estimation interval.

* * * * *